United States Patent
Powell et al.

(10) Patent No.: US 8,004,684 B2
(45) Date of Patent: *Aug. 23, 2011

(54) SENSOR HEAD FOR A DRY POWDER AGENT

(75) Inventors: Brian Powell, Maidenhead (GB); Scott Ayers, Wilson, NC (US)

(73) Assignee: Kidde Technologies, Inc., Wilson, NC (US)

( * ) Notice: Subject to any disclaimer, the term of this patent is extended or adjusted under 35 U.S.C. 154(b) by 210 days.

This patent is subject to a terminal disclaimer.

(21) Appl. No.: 12/421,030

(22) Filed: Apr. 9, 2009

(65) Prior Publication Data
US 2010/0259756 A1  Oct. 14, 2010

(51) Int. Cl.
*G01N 21/00* (2006.01)
(52) U.S. Cl. .......... 356/437; 356/438
(58) Field of Classification Search .......... 356/437–442, 356/627
See application file for complete search history.

(56) References Cited

U.S. PATENT DOCUMENTS

| | | | |
|---|---|---|---|
| 4,758,028 A | 7/1988 | Davies et al. |
| 5,104,735 A | 4/1992 | Cioffi et al. |
| 5,973,774 A | 10/1999 | Haggett |
| 6,122,575 A | 9/2000 | Schmidt et al. |
| 6,181,426 B1 | 1/2001 | Bender |
| 6,819,237 B2 | 11/2004 | Wilson et al. |
| 7,048,068 B2 | 5/2006 | Paulkovich |
| 7,066,274 B2 | 6/2006 | Lazzarini |
| 7,080,793 B2 | 7/2006 | Borisov et al. |
| 7,083,000 B2 | 8/2006 | Edwards et al. |
| 7,087,105 B1 | 8/2006 | Chappell et al. |
| 7,090,028 B2 | 8/2006 | Adiga et al. |
| 7,093,666 B2 | 8/2006 | Trumper |
| 7,104,336 B2 | 9/2006 | Ozment |
| 7,153,446 B2 | 12/2006 | Grigg |
| 7,210,537 B1 | 5/2007 | McNeil |
| 7,232,097 B2 | 6/2007 | Noiseux et al. |
| 7,333,129 B2 | 2/2008 | Miller et al. |
| 7,407,598 B2 | 8/2008 | Posson et al. |
| 7,456,750 B2 | 11/2008 | Popp et al. |
| 7,476,346 B2 | 1/2009 | Hagquist et al. |
| 2010/0257915 A1* | 10/2010 | Ayers .............. 73/1.06 |

(Continued)

FOREIGN PATENT DOCUMENTS

JP  2008017976  1/2008

OTHER PUBLICATIONS

Skaggs R R et al: "Diode Laser Measurements of HF Concentrations from Heptane/Air Pan Fires Extinguished by FE-36, FM-200, FE-36 Plus APP or FM-200 Plus APP", Applied Spectroscopy, vol. 53, No. 9, 1999 pp. 1144-1148.

(Continued)

*Primary Examiner* — Roy Punnoose
(74) *Attorney, Agent, or Firm* — Carlson Gaskey & Olds PC

(57) ABSTRACT

A sensor head for a dry powder agent according to an exemplary aspect of the present disclosure includes a housing defined along an axis along which light is communicated, the housing defines a multiple of apertures transverse to the axis, the multiple of apertures in communication with a measurement volume along the axis. A mirror is within the housing to reflect the light through the measurement volume.

**

U.S. PATENT DOCUMENTS

2010/0259757 A1* 10/2010 Ayers et al. .................. 356/439

OTHER PUBLICATIONS

Gann R G: "Executive Summary" [Online] vol. 1, 1995, pp. 1-4, NIST Special Publication 890, http://fire.nist.gov/bfrlpubs/fire95/pdf/f95059.pdf.

Sheinson R S and Fleming J W: Final Technical Report: Suppression effectiveness of aerosols [Online] Oct. 1, 2003 NIST, Project NGP 2b1; http://www.bfrl.nist.gov/866/NGP/pubs/141_NGP_2b1_Final_Technical_Report.pdf.

European Search Report, dated Jul. 7, 2010, EP 10 25 0750.

* cited by examiner

US 8,004,684 B2

SENSOR HEAD FOR A DRY POWDER AGENT

BACKGROUND

The present disclosure relates to a measurement system for the measurement of dry powder based agents.

In order to certify a dry powder fire suppression system onboard a vehicle such as an aircraft, the agent is discharged into the protected volume and an analyzer simultaneously records the amount of fire extinguishing agent in various zones of the protected volume. The amount of agent must be above some predetermined level which has been established sufficient to extinguish all possible fires for some period of time simultaneous in all zones.

The analyzer must be calibrated and traceable such that analyzer output proves the dry powder fire suppression system is capable of extinguishing any fire within the protected space. No known systems are capable of both measuring aerosol cloud fire extinguishing agent concentrations and being calibrated so as to measure the agent concentration for an aircraft dry powder fire suppression system certification test.

SUMMARY

A sensor head for a dry powder agent sensor head according to an exemplary aspect of the present disclosure includes a housing defined along an axis along which light is communicated, the housing defines a multiple of apertures transverse to the axis, the multiple of apertures in communication with a measurement volume along the axis. A mirror is within the housing to reflect the light through the measurement volume.

A calibration system for a dry powder agent according to an exemplary aspect of the present disclosure includes a powderizer calibration column. A sensor system includes at least one sensor head at least partially within the powder calibration column, the at least one sensor head having a housing defined along an axis along which light is communicated, the housing defines a multiple of apertures transverse to the axis, the multiple of apertures in communication with a measurement volume along the axis. A mirror within the housing reflects the light through the measurement volume. A light source which communicates light into the measurement volume. A receiver to receive reflected light within the measurement volume from the mirror. A control system in communication with the light source and the receiver.

A measurement system for a dry powder agent according to an exemplary aspect of the present disclosure includes a protected structure test fixture. A sensor system includes at least one sensor head at least partially within the protected structure test fixture, the at least one sensor head having a housing defined along an axis along which light is communicated, the housing defines a multiple of apertures transverse to the axis, the multiple of apertures in communication with a measurement volume along the axis. A mirror within the housing reflects the light through the measurement volume. A light source which communicates light into the measurement volume. A receiver to receive reflected light within the measurement volume from the mirror. A control system in communication with the light source and the receiver.

BRIEF DESCRIPTION OF THE DRAWINGS

Various features will become apparent to those skilled in the art from the following detailed description of the disclosed non-limiting embodiment. The drawings that accompany the detailed description can be briefly described as follows.

DETAILED DESCRIPTION

Figure 1:
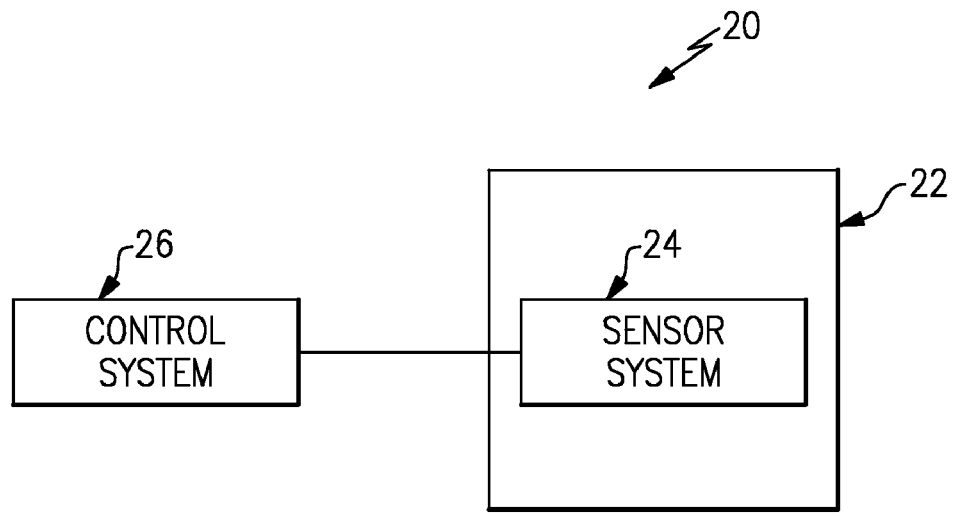
FIG. 1 is a schematic view of a measurement system with a powderizer calibration column (PCC) for a dry powder agent.
Figure 2:
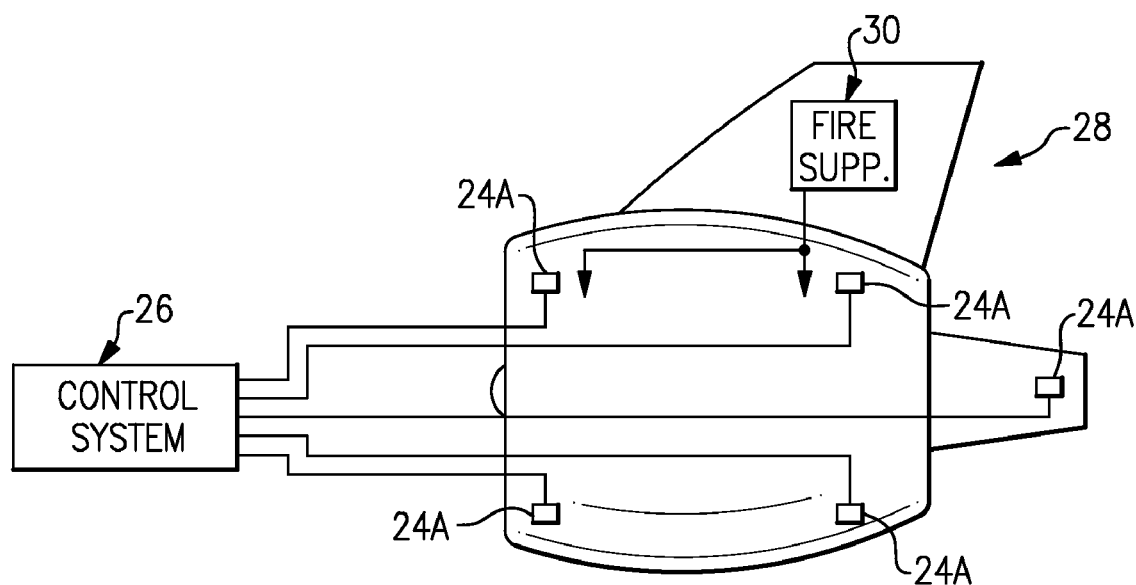
FIG. 2 is a schematic view of a sensor system for a powder based chemical fire suppressant agent installed in a representative protected structure.

FIG. 1 schematically illustrates a measurement system 20 for the measurement of dry powder agent based chemical fire suppressant agents. The system 20 generally includes a powder calibration column (PCC) 22, a sensor system 24, and a control system 26. The PCC 22 generally is utilized to calibrate a sensor of the sensor system 24 which may then be installed in a protected structure test fixture 28 such as an engine nacelle (FIG. 2). It should be understood that the engine nacelle is but one representative structure in one non-limiting embodiment, within which a powder based chemical fire suppressant system 30 may be installed and that other protected structures 28 such as a land vehicle engine compartment, cabin or other structure will also benefit herefrom.

Figure 3A:
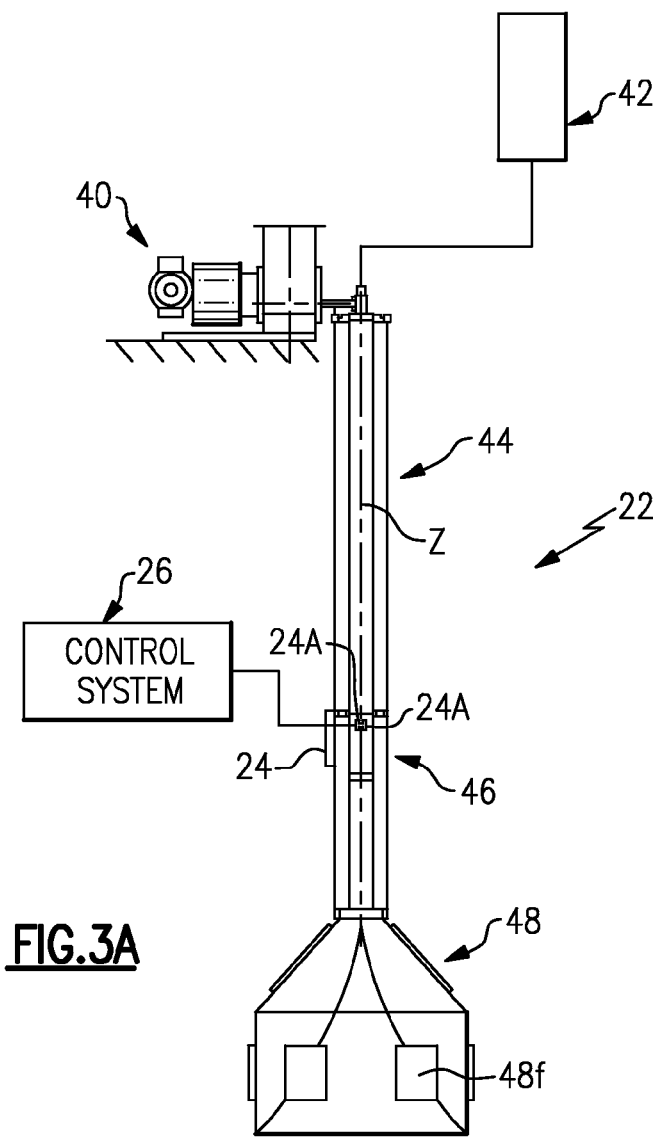
FIG. 3A is a schematic view of a powderizer calibration column (PCC) for a dry powder agent.

Referring to FIG. 3A, the PCC 22 generally includes a powder feeder system 40, a gas distribution system 42, an observation tube 44, a test section 46 within which at least one sensor head 24A, sometimes referred to as a powderizer, is mounted, and a powder capture box 48. The observation tube 44, test section 46 and powder capture box 48 are defined along an axis Z. The observation tube 44 which defines the test section 46 in one non-limiting embodiment is at least twenty diameters in length prior to the at least one sensor head 24A to ensure homogeneous distribution of the powder agent from the powder feeder system 40 and the inert gas from the gas distribution system 42. This facilitates a direct measurement of light transmission through the aerosol cloud by the sensor head 24A.

The powder feeder system 40 in one non-limiting embodiment includes an auger such as that manufactured by Acrison, Inc. of Moonachie, N.J., USA. The powder feeder system 40 defines the rate at which the dry powder agent is communicated into the observation tube 44.

Figure 3B:
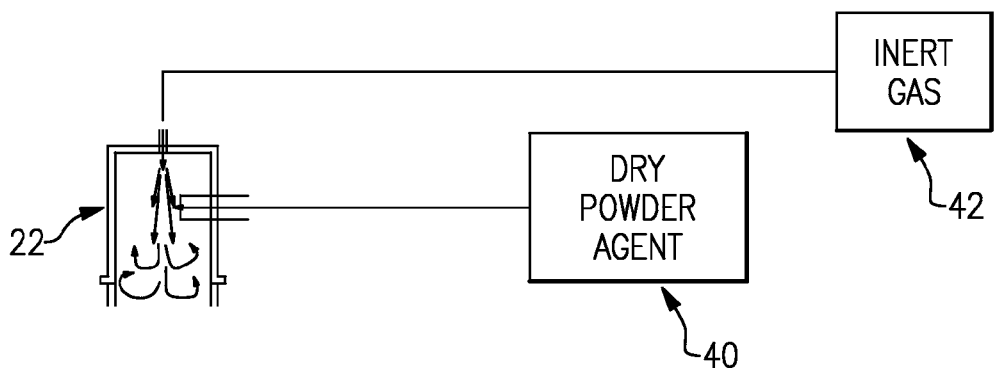
FIG. 3B is a schematic view of a powder feeder system and a gas distribution system for communication with the powderizer calibration column (PCC)

The gas distribution system 42 communicates the inert gas which, in one non-limiting embodiment, includes nitrogen to breakup and fully disperses the dry powder agent. The gas distribution system 42 is located generally above the powder feeder system 40 and transverse thereto (FIG. 3B). The gas distribution system 42 defines the rate at which the inert gas is communicated into the observation tube 44 such that a known flow of dry powder agent and inert gas are received in the sensor head 24A so that a relationship may be determined between the dry powder agent concentration and light transmission. This allows for absolute known rates of dry powder agent feed and inert gas.

The powder capture box 48 provides a relatively large volume to prevent recirculation of the powder agent back into the test section 46. The powder capture box 48 also prevents pressure build up and prevents back flow of the dry powder agent aerosol cloud facilitated by airflow outflow through filters 48F.

The PCC 22 is utilized to calibrate the sensor head 24A light transmission measurement with respect to a concentration of aerosol cloud in mass per volume. The cylindrical cross section of the PCC 22 reduces corner effects and other geometric effects. The dry powder agent is communicated into the observation tube 44 just below the inert gas introduction (FIG. 3B). The high velocity jet of inert gas passes the powder feeder system 40 to cause turbulent mixing of the dry powder agent into the inert gas flow to generate an aerosol cloud as would be typical in an aerosol cloud fire suppression agent. The process which communicates the dry powder agent into the jet of inert gas causes the dry powder agent agglomerates to break up into the principle particles. The particles mixed with the inert gas creates the dry powder agent aerosol cloud.

Figure 3C:
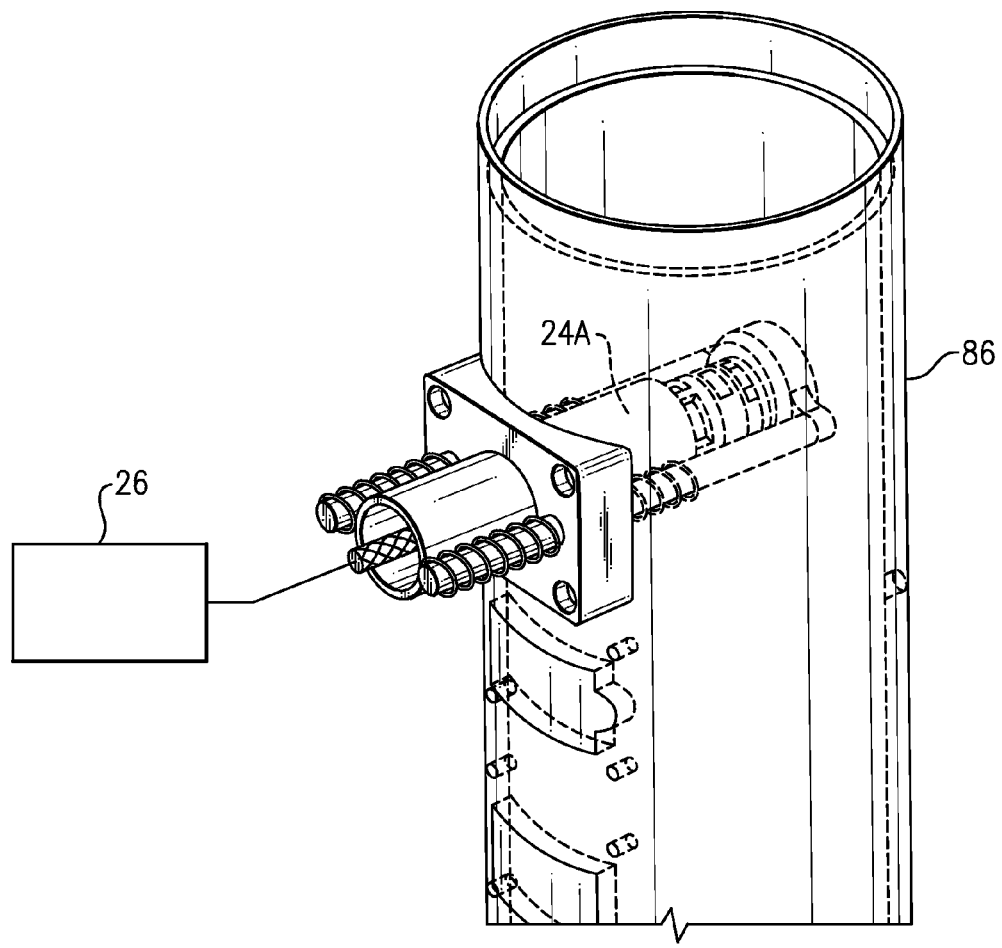
FIG. 3C is a perspective view of a sensor head within the powderizer calibration column (PCC)

The aerosol cloud travels downward with gravity in the observation tube 44 to facilitate homogeneous mixing of the aerosol cloud for measurement by the sensor head 24 (FIG. 3C). The downward flow is necessary because different sized particles of the dry powder agent travel at different velocities. Downward flow at steady conditions results in a steady-state concentration over time as the concentration of each particle size stays constant downstream to allow an accurate measurement by the sensor system 24.

Referring to FIGS. 4A-4D, one non-limiting embodiment of the sensor head 24A provides for a light transmission measurement through the dry powder agent aerosol cloud. Each sensor head 24A includes a housing 50 defined along an axis S though which light is communicated along a light path. The housing defines an aperture 52 transverse to the axis S, a light source 54, a detector 56, a window 58, a mirror window 60 and a mirror 62.

Figure 4A:
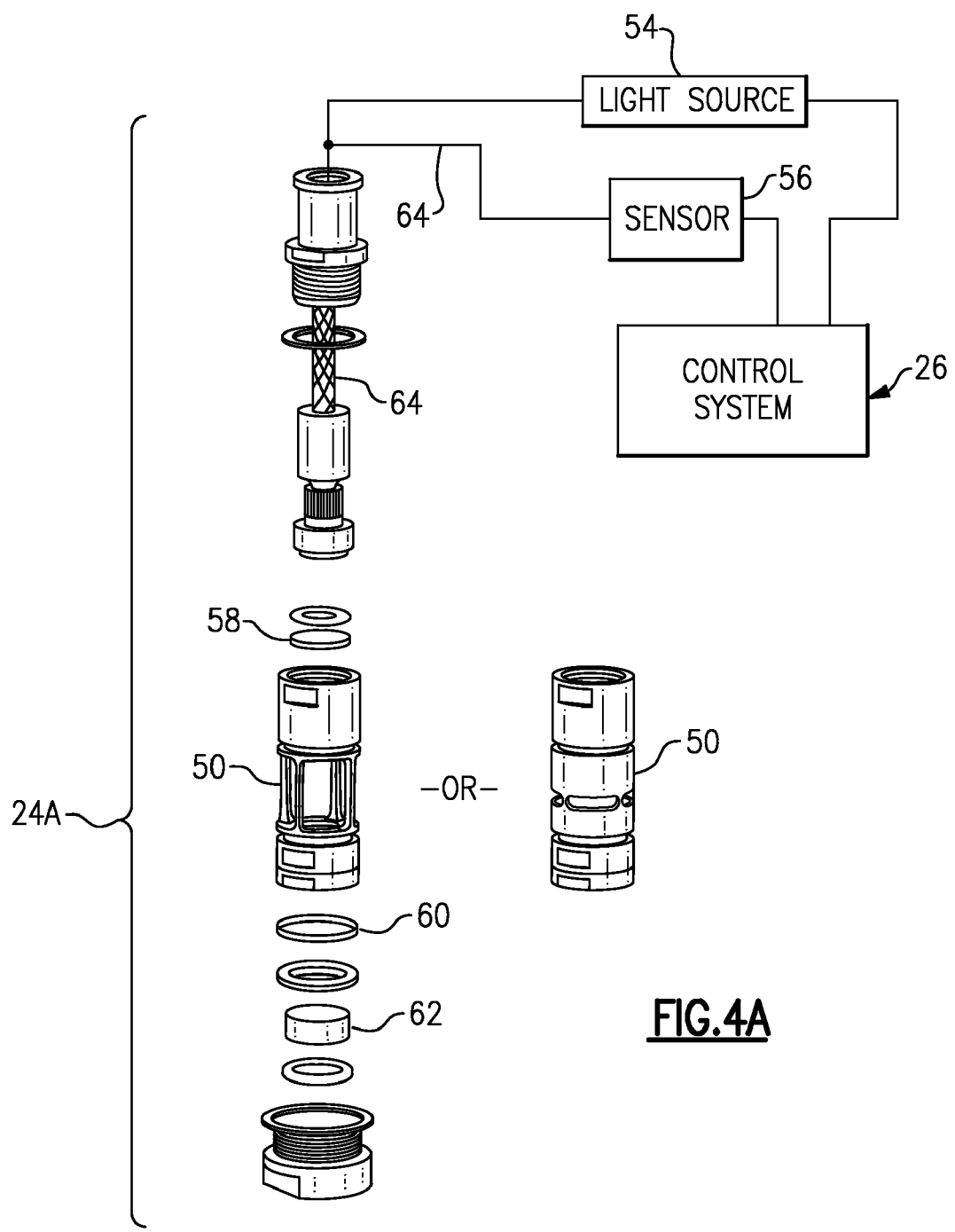
FIG. 4A is an exploded view of a sensor head for a dry powder agent.
Figure 4B:
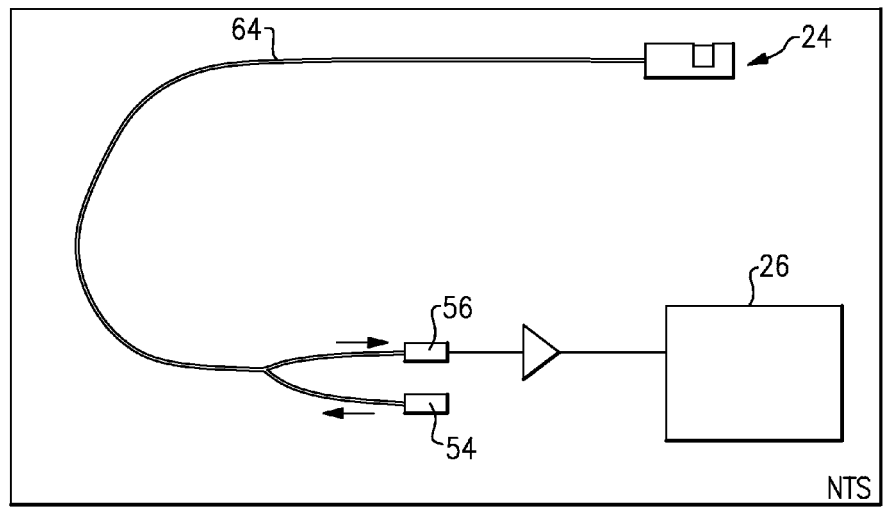
FIG. 4B is schematic view of a sensor head in communication with a control system.
Figure 4C:
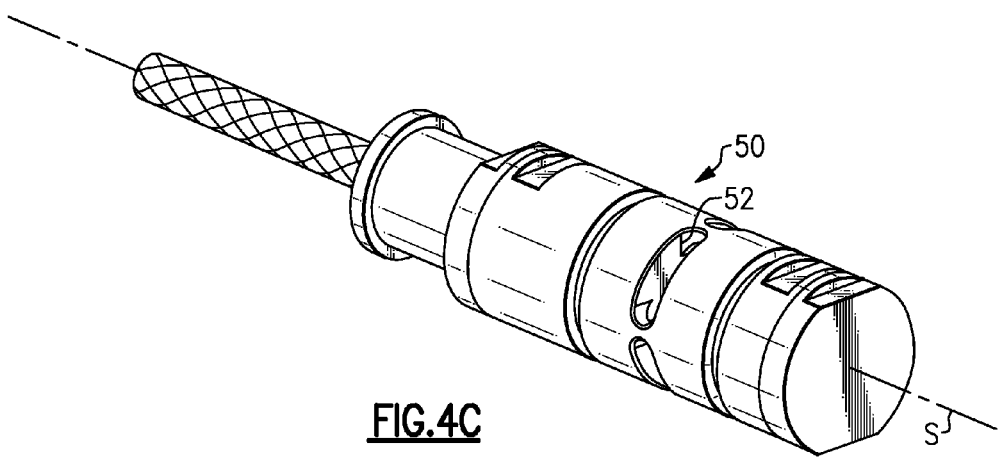
FIG. 4C is a perspective view of one embodiment of a sensor head for a dry powder agent.
Figure 4D:
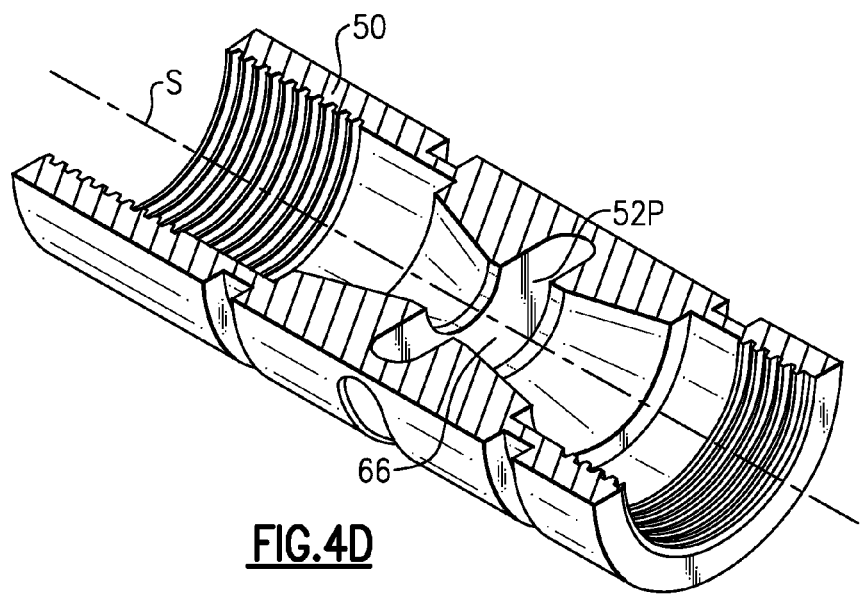
FIG. 4D is a longitudinal sectional view of the sensor head body of FIG. 4C.

The light source 54 in one non-limiting embodiment is a red light emitting diode (LED) operating at 650 nm and the detector 56 is a visible spectrum photodiode. Each sensor head 24A operates on light obscuration principles. Light is communicated from the light source 54 along a fiber optic cable 64, passes through the transparent window 58, enters a measurement volume 66 (FIG. 4D) in communication with the aperture 52, reflects off the mirror 62 and is communicated through the fiber optic cable 64 (FIG. 4B). The window 58 is generally opposite the mirror 62 such that the light passes through the measurement volume 66 twice—from window 58 through measurement volume 66, reflects off mirror 62 then through measurement volume 66 and into the detector 56 via window 58 and the fiber optic cable. The detector 56 outputs an analog signal proportional to the intensity of light to the control system 26. The intensity of light changes functionally to the concentration of dry powder agent particles in the measurement volume 66. The sensor head 24A is unlike thermocouples, pressure transducers, strain gauges or other instrumentation where signal strength is directly related to the phenomena being measured.

Figure 4E:
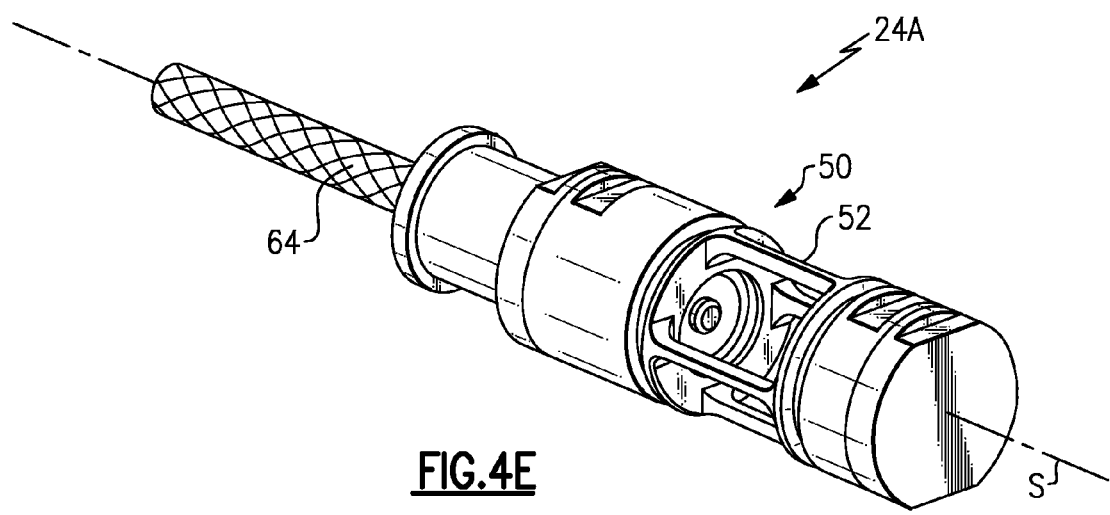
FIG. 4E is a perspective view of another embodiment of a sensor head for a dry powder agent.

Each sensor head 24A of the sensor system 24 is in communication with the control system 26 which initiates operation of the system 20 and controls the data acquisition from the sensor head 24A. Data in one non-limiting embodiment is acquired at a variable frequency of 1 to 1000 Hz for a maximum of 30,000 total points. The maximum acquisition time is 30,000 divided by the acquisition rate (300 seconds in the case of 100 HZ). It should be understood that alternative data acquisition rates may be utilized by the control system 26. In another non-limiting embodiment, the apertures 52' may be of a greater longitudinal length (FIG. 4E).

It should be noted that a computing device can be used to implement various functionality, such as that attributable to the control system 26. In terms of hardware architecture, such a computing device may include a processor, memory, and one or more input and/or output (I/O) device interface(s) that are communicatively coupled via a local interface. The local interface can include, for example but not limited to, one or more buses and/or other wired or wireless connections. The local interface may have additional elements, which are omitted for simplicity, such as controllers, buffers (caches), drivers, repeaters, and detectors to enable communications. Further, the local interface may include address, control, and/or data connections to enable appropriate communications among the aforementioned components.

The processor may be a hardware device for executing software, particularly software stored in memory. The processor can be a custom made or commercially available processor, a central processing unit (CPU), an auxiliary processor among several processors associated with the computing device, a semiconductor based microprocessor (in the form of a microchip or chip set) or generally any device for executing software instructions.

The memory can include any one or combination of volatile memory elements (e.g., random access memory (RAM, such as DRAM, SRAM, SDRAM, VRAM, etc.)) and/or nonvolatile memory elements (e.g., ROM, hard drive, tape, CD-ROM, etc.). Moreover, the memory may incorporate electronic, magnetic, optical, and/or other types of storage media. Note that the memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

The Input/Output devices that may be coupled to system I/O Interface(s) may include input devices, for example but not limited to, a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

When the computing device is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

Figure 5:
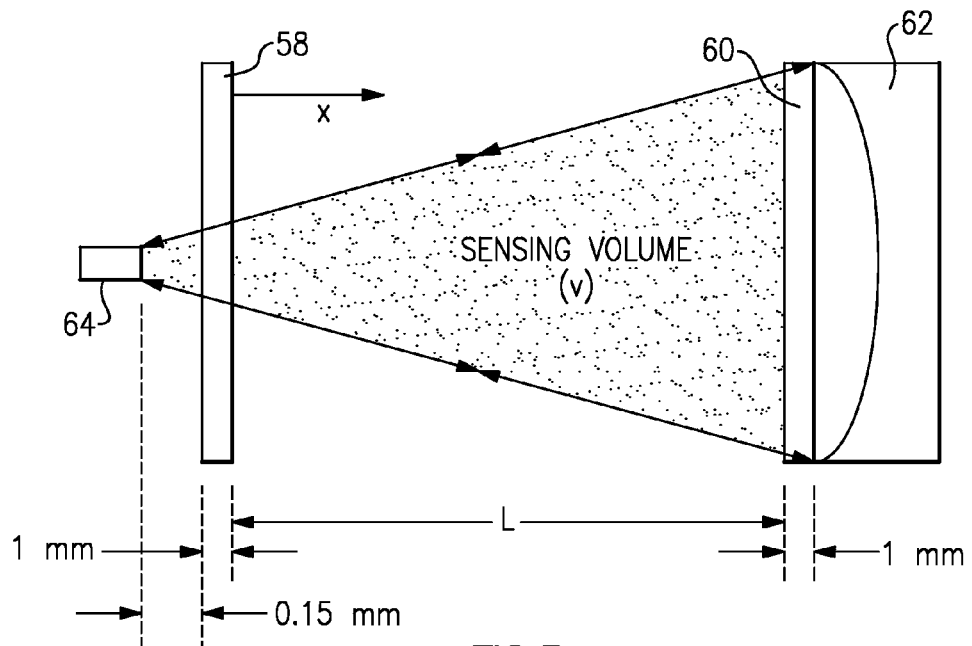
FIG. 5 is a schematic view of a sensor head sensing volume.

Referring to FIG. 5, the sensor head 24A directly measures light transmission though the dry powder agent aerosol cloud, which can be directly related to a spatial mass density concentration via an empirical or theoretical relationship.

The dry powder agent aerosol cloud enters the measurement volume 66 and passes through the light that travels from the fiber optic cable 64 to the mirror 62 and back to the detector 56. As the dry powder agent aerosol cloud passes through the light, the total light transmitted decreases proportional to the concentration of the aerosol cloud. The mirror is concaved and focuses the light back to the fiber optic cable 54.

Figure 6:
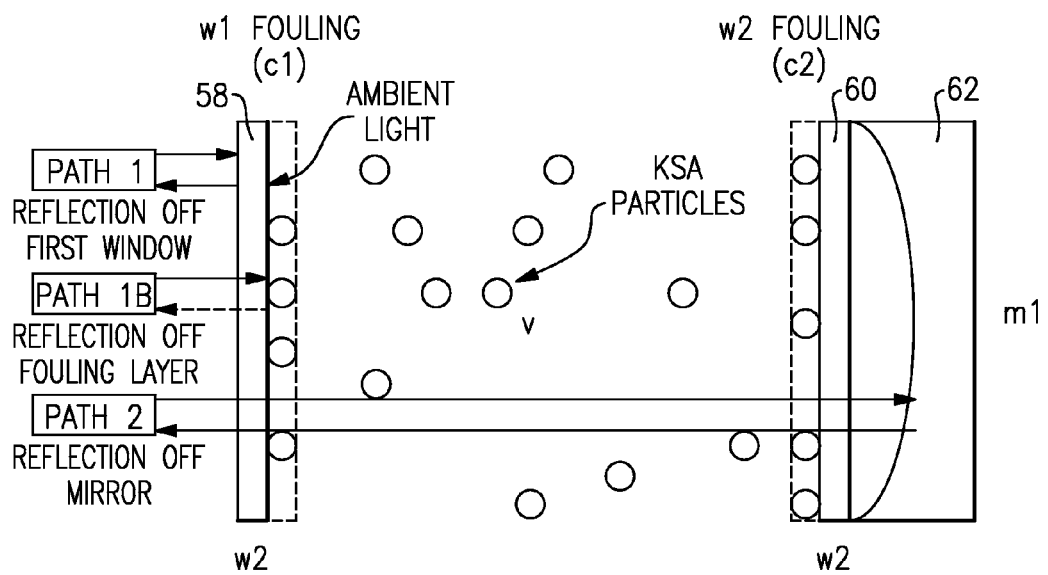
FIG. 6 is a schematic view of a sensor head sensing volume with possible light paths without multiple reflection.

Referring to FIG. 6, representative paths for the light are schematically illustrated. Reflections off of objects beyond the first fouling layer have been ignored due to the insignificant amount of light return. The intensity of light received by the detector 56 is the sum of Paths 1, 1B, 2, and the stray light from the background. In Path 1 some fraction of the reflected light off the window 58 is received. Path 1B occurs if a fouling layer exists on window 58 and must transmit through window 58 twice.

In Path 2, the light must be transmitted twice through each window 58, 60, each fouling layer, the measurement volume 66 then reflects off the mirror 62. The mirror 62 is assumed to reflect all light in these calculations. Both windows 58, 60 have the same properties.

Without a fouling layer, the sensor head 24A output can be expression as:

$$I = f_{w1}\rho_w I_s + \tau_w^4 \tau_{c1}^2 \tau_v^2 \tau_{c2}^2 I_s + I_\infty \quad \text{Equation 1}$$

Prior to a test, the blocked output can be measured setting $\tau_v$ to 0 by blocking the mirror 62 with non-reflective media such that only the light reflected off window 58 and ambient light are measured.

$$I_{bl} = f_{w1}\rho_w I_s + I_\infty \quad \text{Equation 2}$$

The reference value is found when $\tau_v$ is 1, i.e. no aerosol cloud is in the measurement volume and light is allowed to reflect off the mirror back to the source. Substituting in for the measured blocked value:

$$I_{ref} = \tau_w^4 \tau_{c1}^2 \tau_{c2}^2 I_s + I_{bl} \quad \text{Equation 2}$$

By substituting Equation 3 and Equation 2 into Equation 1, the double pass transmittance through the sensing volume during a test can be expressed:

$$\tau_v^2 = \frac{I - I_{bl}}{I_{ref} - I_{bl}} \quad \text{Equation 4}$$

At this point, it is convenient to define a modified sensor head 24A output with the blocked value subtracted off as the blocked value is assumed constant throughout the entire measurement.

$$I^* \equiv I - I_{bl} \quad \text{Equation 5}$$

Equation 4 can be re-expressed:

$$\tau_v^2 = \frac{I^*}{I^*_{ref}} \quad \text{Equation 6}$$

Mass Density Concentration—Theoretical Relationship

The relationship of light transmission to concentration of particles in a dispersed cloud is given by $$\frac{di}{dx} = -n_v''' A_s i \quad \text{Equation 7}$$

Beers' Law, squared here to give the double path transmittance, is a solution to Equation 7 where only the light intensity varies with distance.

$$\tau_v^2 \equiv \left(\frac{i}{i_i}\right)^2 = \exp(-2n_v''' A_s L) \quad \text{Equation 8}$$

Equation 8 can be solved for the number density concentration, when multiplied by the mass of one particle the mass density concentration in the sensing volume is found.

$$m_v''' = \frac{1}{2L}\frac{V_p}{A_s}\rho_s \ln\left(\frac{1}{\tau_v^2}\right) \quad \text{Equation 9}$$

The transmission through the sensing volume term is squared because the light travels through the measurement volume 66 twice. Mie Theory identifies the scattering cross sectional area as approaching twice the particle cross sectional area, as the size of the particle increases from three times the wavelength of light. In this example, the average particle diameter is above 3 μm where the wavelength of the light is 0.65 μm. Because the surface area and the mass of the individual particles are of interest, the Sauter Mean diameter is used. This is the diameter of a particle with the same surface area to mass (volume) ratio as the entire aerosol cloud population. Equation 9 reduces to a function of the Sauter Mean diameter:

$$m_v''' = \frac{1}{3}\frac{d_{[3,2]}}{2L}\rho_s \ln\left(\frac{1}{\tau_v^2}\right) \quad \text{Equation 10}$$

Equation 10 yields a theoretical relationship between the mass density concentration and the transmission if the particle diameter has been characterized. However, this relationship is only valid at high transmissions.

Since the powderizer will measure transmissions less than that valid in Equation 9, the PCC is utilized to derive an empirical relationship between transmission and spatial mass density concentration.

The experiments were conducted in the PCC 22 (FIG. 3A) which provides for constant flows of the dry powder agent and the inert gas. This provides for fully developed flow so that the dry powder agent aerosol cloud is evenly distributed across the observation tube 44 cross section. The fully mixed dry powder agent aerosol cloud then passes by the sensor head 24A where light transmission is measured. By varying the flow rate of inert gas and the feed rate of the dry powder agent, a variety of mass density concentrations could be tested.

The relationship between a transmission and spatial mass density concentration as determined in the PCC is specific to the sensor head 24A design and the dry powder composition and size. If any of these change, a new relationship may be determined.

The measurement error can be found from the scatter in the transmission to spatial mass density concentration data. For the sensor head 24 in FIG. 4C, the error was found to be +/−16 g/m^3. This error would be specific to the sensor head 24 design and the dry powder composition and size.

Figure 7:
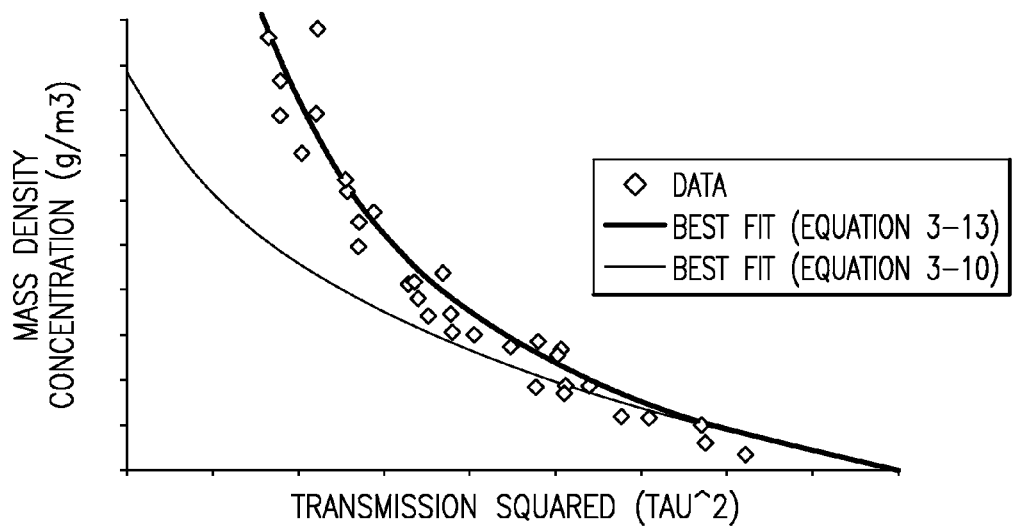
FIG. 7 is an empirical relationship between mass density concentration and light transmittance for a dry powder agent.
Figure 8:
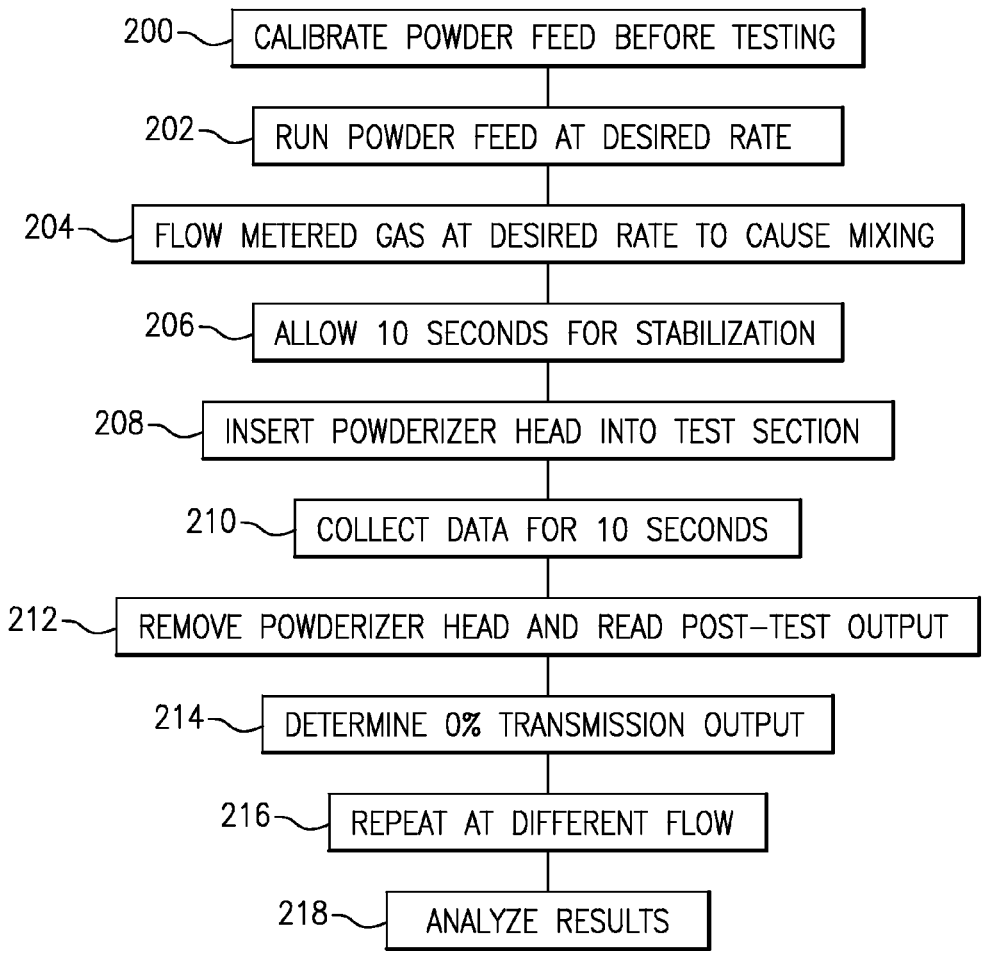
FIG. 8 is a flow chart illustrating calibration of the measurement system to determine an empirical relationship between mass density concentration and transmittance for a desired dry powder agent such as an aerosol cloud fire suppression agent.

Referring to FIG. 8, an operational example of the PCC 20 is illustrated in which the measurement system 20 is operated to determine an empirical relationship between mass density concentration and transmittance for a desired dry powder agent such as an aerosol cloud fire suppression agent (FIG. 7).

In step 200, the powder feeder system 40 is calibrated to a desired dry powder agent rate. The powder feeder system 40 is then operated at the desired dry powder agent rate (g/sec) (step 202) as the gas distribution system 42 is operated at a desired inert gas rate (m3/sec) (step 204) to provide an aerosol cloud mix. A time period is then allowed for stabilization of the aerosol cloud (step 206). The desired dry powder agent rate may include, in one example, from <10 g/m3 to >300 g/m3 which may be obtained by varying auger feed rates and flow rates. The desired inert gas rate may include, in one example, bulk velocities from ~0.5 msec to ~3.5 msec with centerline velocity about 35% greater than bulk velocity.

A sensor head 24A is then inserted into the test section 46 of the PCC 22 (step 208). Data is collected from the sensor head 24A for a predetermined time period (step 210) then the sensor head 24A is removed (step 212). A zero percentage transmission in the PCC 20 from the sensor head 24A is then determined by blocking all light into the sensor head 24A with, for example, a black rubber plug (step 214). Steps 202-214 are then repeated a multiple of times to obtain data points for a curve which represents the empirical relationship between mass density concentration and transmission squared for the desired dry powder agent (Step 218; FIG. 7).

Figure 9:
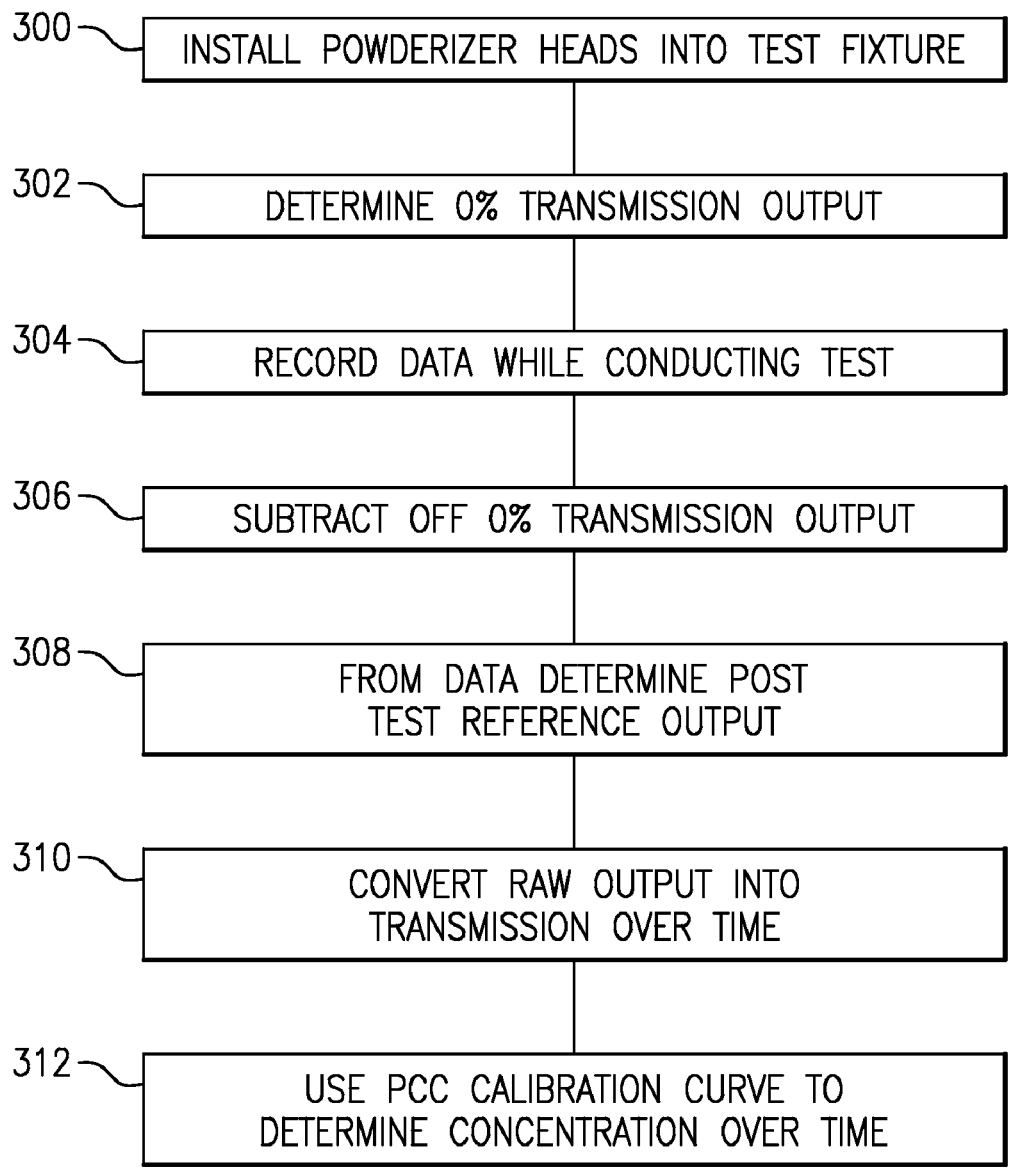
FIG. 9 is a flow chart illustrating operation of the sensor heads located within a protected structure test fixture such as the representative engine nacelle.

Referring to FIG. 9, once the empirical relationship between mass density concentration and light transmittance for the desired dry powder agent (FIG. 7) is determined, one or more sensor heads 24 may be located within a protected structure test fixture 28 such as the representative engine nacelle (FIG. 2).

In step 300, the sensor heads 24 are installed within the desired protected structure test fixture 28. A reference zero percent transmission output is determined for each sensor head 24A (step 302). That is, the difference between the zero percentage transmission in the PCC 20 and the desired protected structure test fixture 28 is determined. The aerosol cloud fire suppression agent is then activated within the protected structure test fixture 28 and data from each sensor head 24A is recorded by the control system 26 during the test (step 304). The reference zero percent transmission output is subtracted for each sensor head 24A (step 306) to determine post test reference raw output (step 308) and convert that raw output into a light transmittance over time (step 310). The sensor head is relatively small so as to be located in a remote compartment so as to measure the light transmittance of the aerosol cloud with respect to time. The light transmittance over time is then utilized with the empirical relationship between mass density concentration and transmittance for the desired dry powder agent (FIG. 7) to determine concentration over time (step 312).

TABLE 2

NOMENCLATURE

| SYMBOL | DESCRIPTION | UNITS |
|---|---|---|
| $A_s$ | Scattering cross sectional area of a particle | $m^2$ |
| d | Diameter | m |
| f | Fraction | — |
| i | Intensity | lux |
| I | Sensor head 24A output | Volts |
| L | Path length of light | m |
| m | Mass | kg |
| n | Number | — |
| V | Volume | $m^3$ |
| x | Dimensional displacement | m |
| ρ | Density | $g/m^3$ |
| $\rho_w$ | Window reflection | — |
| τ | Transmission | — |

NOMENCLATURE

| SUBSCRIPT | DESCRIPTION |
|---|---|
| ∞ | Ambient |
| [3, 2] | Sauter mean |
| bl | Blocked |
| c | Fouling layer |
| i | Initial |
| p | Particle |
| ref | Reference |
| s | Source, Solid, or Scattering |
| v | Sensing volume |
| w | Window |

| SUPERSCRIPT | DESCRIPTION | UNITS |
|---|---|---|
| ''' | Per volume (density concentration) | $1/m^3$ |
| * | Modified sensor head 24A output (blocked output subtracted off) | |

It should be understood that relative positional terms such as "forward," "aft," "upper," "lower," "above," "below," and the like are with reference to the normal operational attitude of the vehicle and should not be considered otherwise limiting.

It should be understood that like reference numerals identify corresponding or similar elements throughout the several drawings. It should also be understood that although a particular component arrangement is disclosed in the illustrated embodiment, other arrangements will benefit herefrom.

Although particular step sequences are shown, described, and claimed, it should be understood that steps may be performed in any order, separated or combined unless otherwise indicated and will still benefit from the present disclosure.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be understood that within the scope of the appended claims, the disclosure may be practiced other than as specifically described. For that reason the appended claims should be studied to determine true scope and content.

What is claimed is:

1. A sensor head for a dry powder agent comprising:
a housing defined along an axis along which light is communicated, said housing defines a multiple of apertures transverse to said axis, said multiple of apertures in communication with a measurement volume along said axis; and a mirror within said housing to reflect said light through said measurement volume.

2. The sensor head as recited in claim 1, wherein said light is sourced from a red light emitting diode.

3. The sensor head as recited in claim 2, wherein said light emitting diode operates at 650 nm.

4. The sensor head as recited in claim 1, further comprising a light source which communicates light into said measurement volume through a fiber optic cable.

5. The sensor head as recited in claim 4, further comprising a lens located opposite said mirror, said lens in communication with said fiber optic cable.

6. The sensor head as recited in claim 5, further comprising a sensor located opposite said mirror, said sensor in communication with said fiber optic cable.

7. The sensor head as recited in claim 1, wherein each of said multiple of apertures are 3 mm along said axis.

8. The sensor head as recited in claim 1, wherein each of said multiple of apertures are 17 mm along said axis.

9. A calibration system for a dry powder agent comprising:
a powderizer calibration column;
a sensor system which includes at least one sensor head at least partially within said powder calibration column, said at least one sensor head comprises:
a housing defined along an axis along which light is communicated, said housing defines a multiple of apertures transverse to said axis, said multiple of apertures in communication with a measurement volume along said axis;
a mirror within said housing to reflect said light through said measurement volume;
a light source which communicates light into said measurement volume;
a receiver to receive reflected light within said measurement volume from said mirror; and
a control system in communication with said light source and said receiver.

10. The system as recited in claim 9, wherein said control system is in communication with said light source and said receiver through a fiber optic cable attached to said housing.

11. The system as recited in claim 9, wherein said control system is operable to determine an empirical relationship between a mass density concentration and a light transmittance for the dry powder agent.

12. The system as recited in claim 9, wherein said control system is operable to calibrate said at least one sensor head.

13. The system as recited in claim 9, wherein said control system is operable to calibrate said at least one sensor head light transmission measurement to a mass density concentration of an aerosol of the dry powder agent.

14. The system as recited in claim 9, wherein said control system is operable to calibrate said at least one sensor head light transmittance measurement to a concentration of an aerosol of the dry powder agent within said powderizer calibration column in mass per volume.

15. A measurement system for a dry powder agent comprising:
a protected structure test fixture;
a sensor system which includes at least one sensor head at least partially within said protected structure test fixture, said at least one sensor head comprises:
a housing defined along an axis along which light is communicated, said housing defines a multiple of apertures transverse to said axis, said multiple of apertures in communication with a measurement volume along said axis;
a mirror within said housing to reflect said light through said measurement volume;
a light source which communicates light into said measurement volume;
a receiver to receive reflected light within said measurement volume from said mirror; and
a control system in communication with said light source and said receiver.

16. The system as recited in claim 15, wherein said control system is operable to measure a concentration of an aerosol of the dry powder agent within said a protected structure test fixture.

17. The system as recited in claim 16, wherein said protected structure test fixture is a gas turbine engine nacelle.

18. The system as recited in claim 15, wherein said protected structure test fixture is a gas turbine engine nacelle.

* * * * *